(12) United States Patent
Klucha

(10) Patent No.: US 9,797,810 B2
(45) Date of Patent: Oct. 24, 2017

(54) CYCLE FRAME FATIGUE AND DURABILITY ASSEMBLY

(71) Applicant: MSH1 LLC, Colchester, CT (US)

(72) Inventor: Matthew P. Klucha, Colchester, CT (US)

(73) Assignee: MSH1 LLC, Colchester, CT (US)

( * ) Notice: Subject to any disclaimer, the term of this patent is extended or adjusted under 35 U.S.C. 154(b) by 3 days.

(21) Appl. No.: 14/838,119

(22) Filed: Aug. 27, 2015

(65) Prior Publication Data

US 2017/0059461 A1   Mar. 2, 2017

(51) Int. Cl.
  *G01M 17/007* (2006.01)
  *B62K 19/06* (2006.01)
  *B62K 19/16* (2006.01)

(52) U.S. Cl.
  CPC .......... *G01M 17/007* (2013.01); *B62K 19/06* (2013.01); *B62K 19/16* (2013.01); *G01N 2203/0037* (2013.01); *G01N 2203/0073* (2013.01)

(58) Field of Classification Search
  CPC ..................................................... G01N 3/02
  USPC ........................................................ 73/788
  See application file for complete search history.

(56) References Cited

U.S. PATENT DOCUMENTS 5,165,278 A * 11/1992 Huszczuk .............. A61B 5/221
  482/900

FOREIGN PATENT DOCUMENTS

| CN | 203224365 U | * 10/2013 | |
| ES | EP 2669062 A1 | * 12/2013 | ........... B25H 1/0014 |
| SU | 1437724 A1 | * 11/1988 | |

OTHER PUBLICATIONS

Google translation of CN 203224365 U.*

* cited by examiner

*Primary Examiner* — Lisa Caputo
*Assistant Examiner* — Nathaniel T Woodward
(74) *Attorney, Agent, or Firm* — Damian Wasserbauer, Esq.; Wasserbauer Law LLC

(57) ABSTRACT

An assembly, system and method is disclosed for measuring fatigue and durability of a bicycle frame by applying and measuring a precise input of force to a frame. The system of the present invention is configured to measure failure points of different constructions and size of bicycle frames including carbon fiber, aluminum and steel frame constructions.

2 Claims, 4 Drawing Sheets

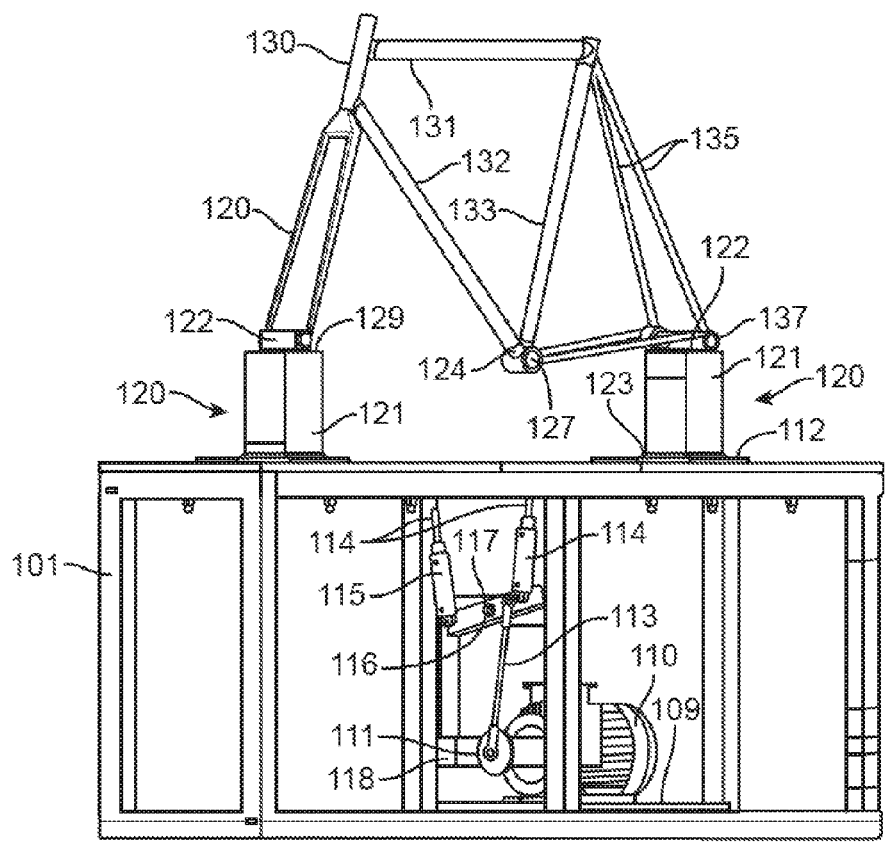
FIG. 3
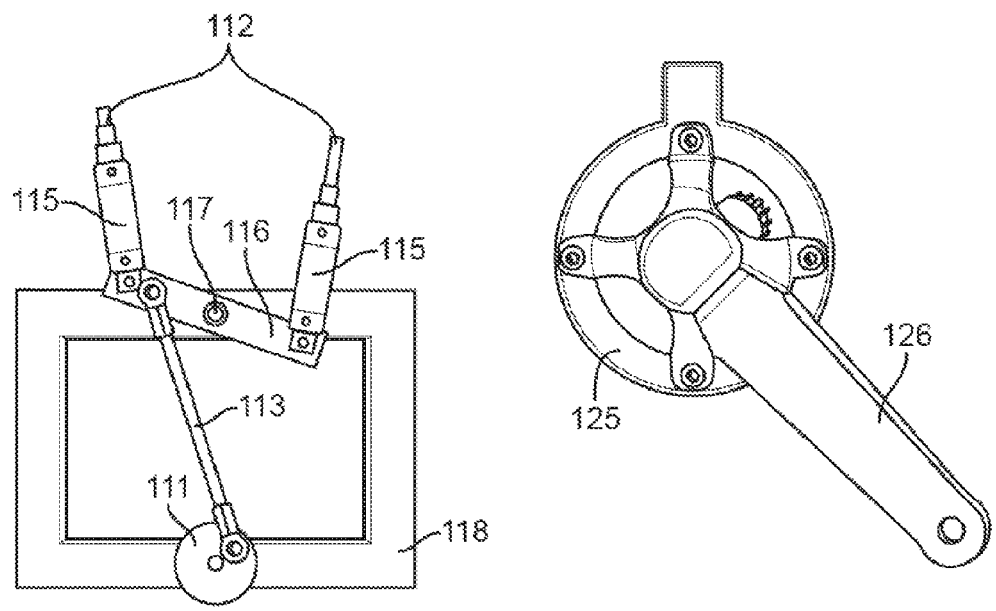
FIG. 4
FIG. 5

CYCLE FRAME FATIGUE AND DURABILITY ASSEMBLY

FIELD OF THE INVENTION

The present invention relates to a standard setting assembly, system and method adapted to apply a precise input of force to a frame for measuring fatigue and durability.

BACKGROUND OF THE INVENTION

The purchase of a bicycle currently involves aligning the cost, use and desired longevity. For example, a racer may desire a superlight-weight bike frame without need for longevity, whereas another consumer may weight differences in cost and construction such as between a steel, aluminum and composite frame. Currently there is no alignment of cost and longevity whereby the consumer could measure and understand what they are buying.

It is desirable to provide a standard that measures a steel, aluminum, and composite frame in overall life expectancy terms. The "Full Disclosure" for a frame overall life expectancy is useful to the consumer in determining what to expect for intended use for the purchase price. For example, metal frames are more tolerance to damage (i.e. metals tend to bend but not break), whereas the laminates of composite frames may fail as minor imperfections are amplified into cracks that propagate and lead to consequences of failure.

SUMMARY OF THE INVENTION

It is an object of the present invention to provide an apparatus, system and method of measuring in overall life expectancy terms the number of cycles a frame (i.e. a steel, aluminum, DUR, and composite frame, etc.) will go through before it fails.

It is an object of the present invention to provide an apparatus, system and method to apply input of force applied at the pedal to measure the number of cycles to fatigue (i.e. # cycles to fatigue).

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations, wherein:

FIG. 3 illustrates an perspective end view of the frame test assembly;

FIG. 4 illustrates an perspective end view the motor linkage of the assembly; (pdf file "Sheets_4_FIGS. 1-7.pdf page 3:" "FIG. 4" is missing FIG. 5 illustrates an side view a crank used in the frame testing assembly;

DESCRIPTION OF THE EMBODIMENTS

Figure 1:
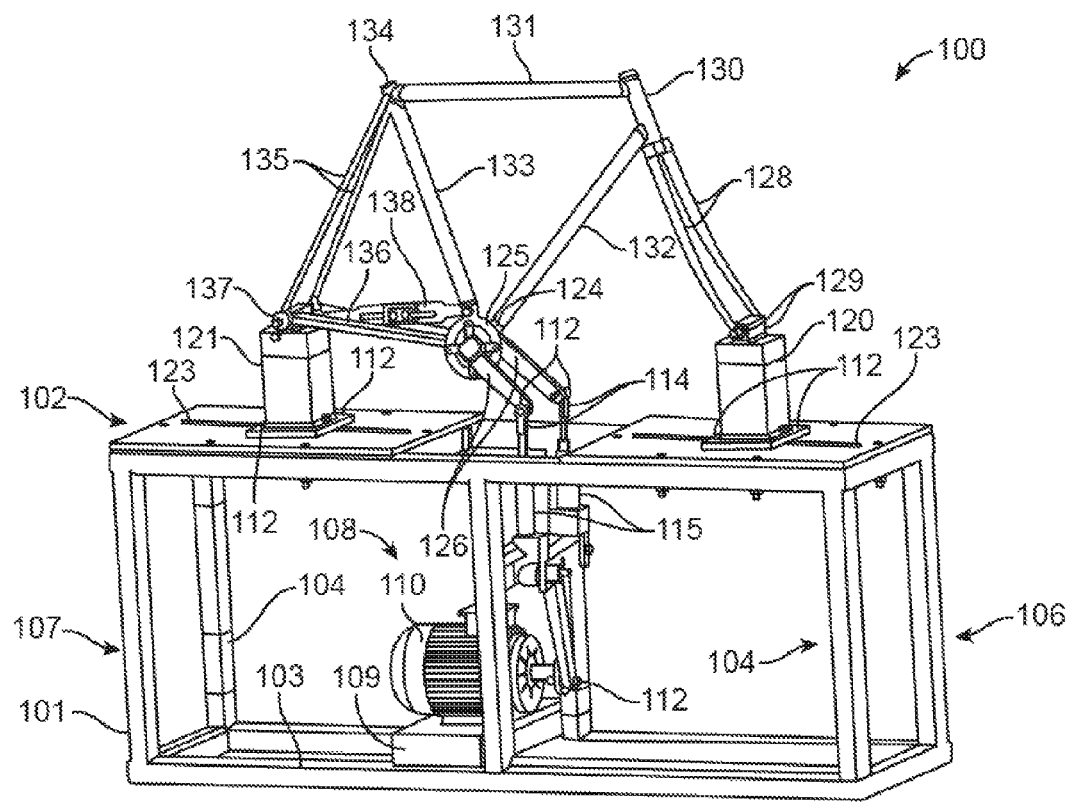
FIG. 1 illustrates schematic perspective view of a frame test assembly, system, and method in accordance with an embodiment of the present invention.
Figure 2:
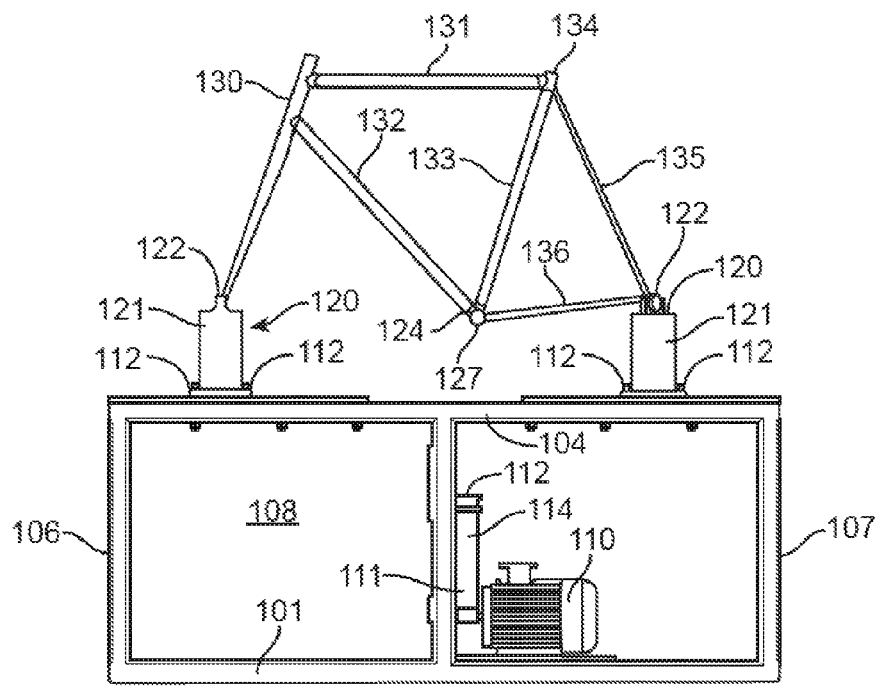
FIG. 2 illustrates a side view of the frame test assembly.
Figure 6:
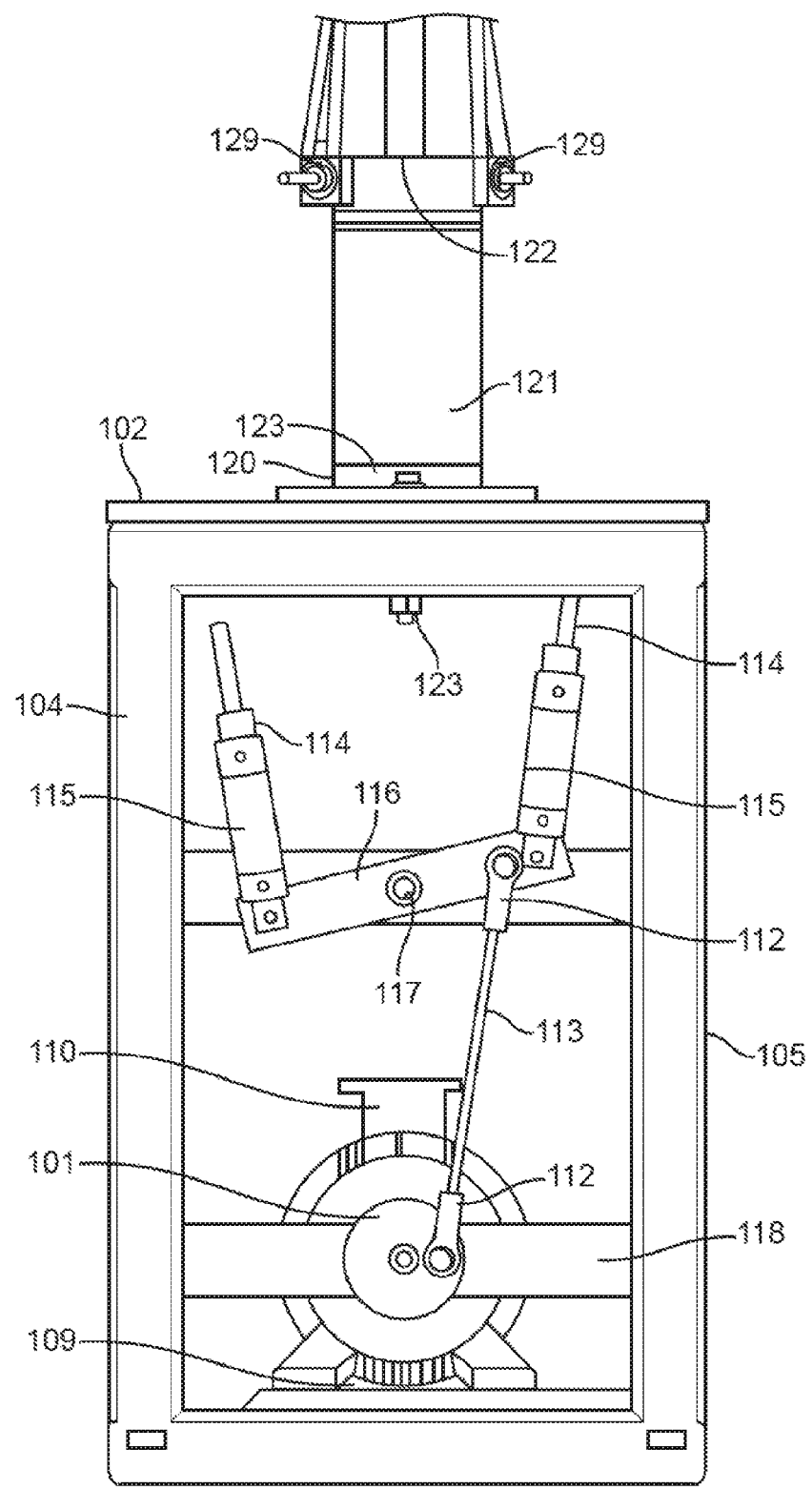
FIG. 6 illustrates an end view the motor linkage of the assembly.
Figure 7:
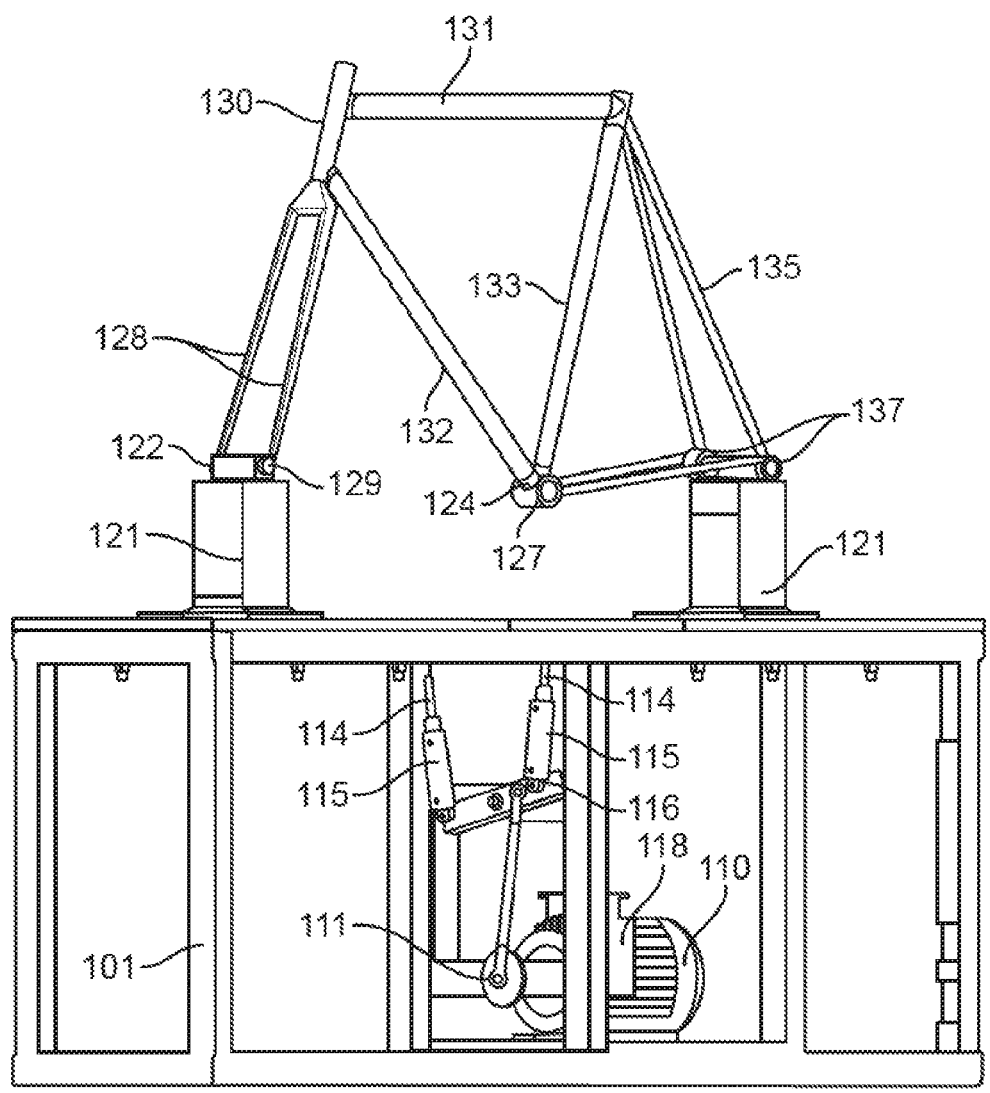
FIG. 7 illustrates an perspective view of the assembly.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As is illustrated in FIGS. 1 through 7, an apparatus, system and method of testing and validating the number of cycles ("#cycles to fatigue") a bicycle frame will go through before it fails is referred to generally by element 100. Historically, the tubes of the frame have made of steel. Steel is still used, while frames can also be made from materials such as aluminum alloys, titanium and carbon fiber. Several properties of a material help decide whether it is an appropriate in the construction of bicycle frame. A universal frame stress test is not presently known; although such a standard frame stress test would be extremely useful (1) for bicycle manufacturer's to verify claims of stiffness and longevity as well as for (2) the consumer purchasing a bicycle so as to be able to purchase correctly a frame suitable to the consumer's needs such as, for example, balancing between weight, performance, longevity and purchase price. It is known in manufacturing that imperfections can occur that can initiate the propagation of the imperfection to result in failures during use. Imperfections in lugged steel frames may occur at the brazed joints, whereby and TIG welded steel, aluminum and titanium alloy frame failures typically occur by within the heat affected zone of the weld, particularly if the entire frame is not annealed and then properly heat treated. Imperfections in composite frames can occur anywhere (i.e. not just at the joint as the joints and connections are fairly well wrapped) and failures typically occur by deformation and/or de-lamination and/or crack/imperfection propagation.

Referring to FIGS. 1-4, the assembly and system 100 is utilized to test frame stress (i.e. a bicycle frame made from steel, aluminum or composite) for the construction, for the joints, tubes, and for the fittings of the frame. As shown in FIGS. 1 through 7, a conventional diamond frame design is made of two triangles, a main triangle and a paired rear triangle, whereby the main triangle consists of the head tube 130, cross bar or top tube 131, down tube 132 and seat tube 133. The rear triangle consists of the seat tube 133, and paired seat stays 135 and paired chain stays 136. As used herein the term "frame" refers to a bicycle frame; however, it is contemplated that the test rig and principals can be utilized for fatigue and durability tests for other frames such as moped, motorcycles, etc. The main component of a bicycle is the frame onto which wheels and other components are fitted.

More specifically, the bicycle frame construction has a head tube 130 containing the headset or otherwise the interface with the fork 128 that has front drop outs 129. The top tube 131 connects the head tube 130 to the seat tube 133 at the top, and the down tube 132 connects the head tube 130 to the bottom bracket 127 where the center lug 124, the chain wheel 125, and crank or pedal arms 126 are attached. The rear triangle connects to the rear dropouts 137, where the rear wheel is attached, and consists of the seat tube 133 and paired seat stays 135 and chain stays 136. The chain stays 136 run parallel to the chain, connecting the bottom bracket 127 to the rear dropouts 137. The seat stays 135 connect the top of the seat tube 133 (often at or near the same point as the top tube) to the rear dropouts 137.

Accordingly, in most conventional steel frame construction uses standard cylindrical steel tubes connected with lugs for both road bicycles and mountain bicycles. Lugs are fittings made of thicker pieces of steel. In one method of construction, the tubes are fitted into the lugs, which encircle the end of the tube, and are then brazed to the lug (i.e. silver brazing in particular) where the frame tubes are precisely aligned into a jig and fixed in place until the brazing is complete. In another method TIG & MIG welding of bicycle frame construction is a possible use cylindrical steel tubing connected by TIG welding or brazed (fillet) welding, which does not require lugs to hold the tubes together, where the frame tubes are precisely aligned into a jig and fixed in place until the welding is complete.

Also steel frames may be constructed using butted tubing that reduces weight and increases cost. The term "butting" means that the wall thickness of the tubing changes from thick at the ends (for strength) to thinner in the middle (for lighter weight). In yet another construction variation, modern tubing is made of special steel alloys (generally chromium-molybdenum, or "chromoly" steel alloys) chosen for their combinations of strength and lightness. One of the most successful older tube types was manganese alloy tube such as Reynolds "531". Furthermore, very lightweight aluminum alloys can be used but may perform badly inadequately to repetitive flexing it will fail through a process called fatigue (i.e. the tube will crack, then fracture). For example, if too much flexion is demanded of aluminum it will fatigue, unlike some steel alloys, and failure can occur completely and without warning to the dismay of the cyclist (consumer). The most popular type of aluminum alloy tube construction connects tubes together by Tungsten Inert Gas (TIG) welding. Moreover, in contrast to some steel and titanium alloys which have a fatigue endurance limit, composites and aluminum have no fatigue endurance limit, and if cracking is not identified even the smallest repeated stresses will eventually cause failure if repeated enough, of course, again to the dismay of the cyclist (consumer).

Finally, titanium bicycle frame tube construction is exotic and expensive although it combines many desirable characteristics: a high strength to weight ratio, excellent corrosion resistance, and stiffness (roughly half that of steel) that allows titanium frames to be constructed with "standard" tube sizes. Titanium frame tubes are typically joined by Tungsten inert gas welding (TIG) and may be joined by vacuum brazing. As many titanium frames can be much more expensive than similar steel alloy frames, cost can put them out of reach for many cyclists. Many common titanium alloys and even specific tubes were originally developed for the aerospace industry. Titanium alloys which have a fatigue endurance limit and the frame will fail if the limit is reached, of course, again to the dismay of the cyclist (consumer).

Composite materials (i.e. carbon fiber) may be used for bicycle frame tubes. Carbon fiber is a non-metallic material that, although expensive, it has light weight, corrosion resistance and high strength, and can be formed in almost any shape desired. The result is a frame that can be fine-tuned for specific strength where it is needed (to withstand pedaling forces), while allowing flexibility in other frame sections (for comfort). Custom carbon fiber bicycle frames may be formed with individual tubes strong in one direction (such as laterally), while compliant in another direction (such as vertically). Typically, carbon fiber frames are constructed by assembling cylindrical tubes in the desired shape and joining these tubes with adhesives and lugs, in a method somewhat analogous to a lugged steel frame. More exotic carbon fiber frames may be manufactured in a single piece (i.e. monocoque construction). Consequently, in contrast to metal frame construction, while composite materials provide light weight and strength, they have a limited fatigue life and fail due to: (1) a much lower impact resistance; (2) are prone to damage from hazard impact, if crashed or mishandled; and (3) are vulnerable to fatigue failure, a process which occurs over a long period of time.

All of these constructions may be bewildering to the consumer deciding on whether to purchase a composite or metal bicycle frame. There is no standard measure of the fatigue and durability of the frames; although, many manufacturer's may make general claims to stiffness and durability. Moreover, as opposed to other consumer purchases, the price of the construction does not reflect durability and longevity because the cost of the composite or metal frame can simply be due to a more expensive construction process and material list. While this may not be a factor for a "racer" who purchases a specialty racing bicycles built for competition (e.g. team racing, individual time trial races and triathlons) because in may in fact be to advantage the cyclist to compete in a race or to advantage an individual cyclist to attain maximum speed that consequently outweigh other considerations. As a result, it would be an improvement in the manufacture, marketing and sale of composite and metal bicycle frames to have a standard measure of the failure limits and longevity of bicycle frames according to a standard scale.

Accordingly, there is a long-felt need for an apparatus, system and method of testing and validating the number of cycles ("#cycles to fatigue") a bicycle frame will go through before it fails. In an embodiment of the present invention, a precision test station can test and validate the number of cycles a frame will go through before it fails using a known input of force applied at the pedal. A standard measure and scale can be established to review bicycle frame fatigue and durability to broadly assess various companies' composite and metal bicycle frame constructions so as to provide a guide for the consumer to make a bicycle frame purchasing decision. For example, a scale may be formed to measure:

Lifespan
  Test to fatigue
Tolerance to Test damage applied to frame
  Resulting cycle life
Back to back testing of perfect frame
  Life happens, damage wear out, from impacts,
Fatigue life (i.e. carbon reduced by factor of 4×, v steel unaffected)

In this manner a guide to inform the consumer based on the standardization of the measured performance of a composite or metal frame allows the consumer to make a bicycle frame purchasing decision on what may happen, the frame expected lifespan (i.e. without damage due to crashes or impacts), and to know the risks of a particular construction of a composite or metal frame. In this manner, the consumer may be motivated to make different decision at onsite that is not related to the cost of the bicycle but according to the performance reflected in the standard measure of the present invention.

Referring to FIGS. 1-4, the assembly and system 100 includes a stand 101 configured in a generally rectangular reinforced cube. The construction of the stand 101 can be of welded aluminum square tubing functioning to be solid and stiff functioning so as to not affect the testing of the bicycle frame. The stand 101 has a top surface 102, a bottom surface 103 which can have friction material or rubber mounts secured thereto (e.g. dampening vibration, sound and to prevent movement relative to the floor), sides 104, 105 and ends 106, 107. The stand 101 may be formed with an inner or internal void 108 and a mounting plate 109 for securing a motor 110 thereto. The motor 101 can be an electric or other motor such as, for example, ½ horse power, electric 1750 RPM motor. The motor 110 can be attached to a gear or transmission to gear-down the motor in a ration of 10:1 to simulate bicycle conditions (i.e. reducing cycles to 175 RMP from 1750 RPM). The motor 110 can be attached to the mounting plate 109 by suitable fasteners 112.

Referring to FIGS. 1, and 3-6, the transmission 111 is connected at one end to a crank arm 113 and at the other end to a connector bar 116 mounted by a pivot 117 to a square mount 118 that is attached to the stand 101 at a predetermined location (i.e., below the bottom bracket 127 of the bicycle frame mounted for testing). The connector bar 116 two air cylinder pistons 115 attached thereto. The pistons 115 are connected upwardly extending arms 114. The arms 114 provide macro and fine adjustments to connect the pistons and motor 110 to the to the bicycle frame via each crank or pedal arm 126. The arms 114 are poles with a locking surface (i.e., have knurled surfaces) to provide small enough adjustments to be within a small adjustment dimension. The pistons 115 are selected to provide fine adjustments so as to precisely balance the forces applied to the bicycle frame via each crank or pedal arm 126. The pistons provide infinite adjustments on air cylinder itself to reach perfectly balanced condition. The balanced condition is important to provide a uniform load to the critical area (i.e. the crank arm, bottom bracket 127, down tube 132, seat tube 133) when testing this critical area in composite and metal (e.g. steel, aluminum and titanium tube) bicycle frame constructions, as well as to the entire bicycle frame. In another aspect of the present invention, the apparatus, system and method can be used in the design of a new bicycle frame so as to reapply the same forces after making a change in configuration so as to design the new bicycle frame to see how it is affected by forces applied at the pedal arm 126 as well as durability in how the bicycle frame performs.

The top surface 102 has a mounting assembly 120 secured thereto by fasteners 112. The mounting assembly 120 is configured to mount the bicycle frame to the stand 101. The mounting assembly may be formed with one or more pillars 121 having lug mounts 122 at an upper portion thereof. The lug mounts 112 are configured to secure the bicycle frame at the front drop out 129 of the fork 128 and secure to the rear drop out 137 at the apex of the seat stay 135 and chain stay 136. The bicycle frame front drop out 129 and rear drop out 137 can be secured to the lug mounts 122 with suitable fasteners 112 (e.g. bolts and nuts). The mounting assembly 120 can be configured with a track 123 in the top surface 102 adapted to adjust the location of the pillars 121 so as to position the mounting of the front drop out 129 and rear drop out 137 to the lug mounts 122 for various size bicycle frames. As shown in FIG. 1, and as discussed herein, once the bicycle frame is mounted in the mounting assembly, the pedal arm 126 can be secured to the motor 110 via the transmission 111, crank arm 113, connector 116, air cylinder 117, and arms 114 as well as being established in a balanced condition by making adjustments to the air cylinder 117, and arms 114. A Chain Tensioner 138 is attached between 125 and 137, to prevent rotation of 125, and link the 137 in the fashion to simulate a chain on a bicycle.

In operation, the present invention provides a method of testing 100 to provide a guide for the consumer. Each bicycle frame can be tested with the same, standardized apparatus and system 100, thereby providing the industry a useful standardized rig and process to validate bicycle frames that fatigue and durability can be published. The bicycle frame to be tested is mounted to the mounting assembly 120 and the stand 101. The pedal arms 126 are established in a 45 degree downward orientation, which is the location of the largest force (greatest stress) to the bottom bracket 127 during pedaling by the cyclist. This position is then secured with the chain tensioner arm 138. The arms 114 are securely connected to the pedal arms 126 by suitable fasteners 112. The arms 114 are adjusted to a measured balanced condition via indexed adjustable connectors attached to Pivot Lever Arm 116 in a horizontal position on pivot 117. Fine adjustments may be made to the air cylinders 115 to bring to a precisely equally balanced condition. When energized the motor 110 provides a predetermined force input to each pedal arm 126 and the # cycles to fatigue can be counted by suitable means. Upon fatigue and failure, the measured results are recorded for the particular bicycle frame along with its make, model, construction and composition (i.e. composite or metal tube frame). In this manner the consumer's purchase decision may be one which is informed and aligned with quality and expected life span of device buying and "Full Disclosure" can be provided to consumer as to what they are buying in the bicycle frame relative to other bicycle frames. The standard test will apply a load equal to twice the power output of a professional cyclist who produces 600 Watts. The number of cycles the frame endures prior to failure will be tallied. The mode of failure, and area of failure will be tallied. This number of cycles to fatigue failure number will be used to formulate a meaningful ranking quotient that the customer can use to compare expected life of a frame relative to other frames on the market. Also information regarding failure mode, and area of failure can be provided as well to provide the necessary information to the customer regarding where the most vulnerable part of the frame is, such that they may perform regular inspections of these particular area(s) for signs of cracks, delamination, damage, or impending failure. This information will be published along with other published data included in a bicycle specification such as weight, and frame geometry. The ranking quotient will be called (something like) Relative Expected life number. The simple comparison will help guide the customer on what to expect in terms of life expectancy for the frames under their consideration. They can then use the "Relative Expected Life Number" in their decision process in unison with other factors which normally guide customer decision such as weight. Oftentimes customers buy a bike solely because of its light weight, when often what they need is a reliable and long lasting frameset.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An assembly for rating a bicycle frame, comprising:
   a stand configured with an internal void and a mounting plate for securing a motor thereto,
   a mounting assembly operably coupled to said stand for securing the bicycle frame thereto, said mounting assembly being disposed above said mounting plate and motor;
   a transmission assembly operably coupled to said motor so as to gear-down revolutions of said motor in a ratio of 10:1 to simulate bicycle conditions;
   a crank assembly comprising pedal arms operably connected to said transmission assembly, each of said pedal arms being connected at one end to said transmission assembly in a fixed angular position and at the other end to a connector bar mounted by a pivot to a square mount attached to said stand below a bottom bracket of the bicycle frame mounted for testing; and
   one or more pistons operably connected to said pedal arms so as to provide macro and/or fine adjustments to connect said one or more pistons and said motor to the bicycle frame via each of said pedal arms,
   whereby when said motor is energized to provide a predetermined force input to each of said pedal arms so as to fatigue the bicycle frame such that the number of cycles to fatigue can be counted.

2. A system for rating a bicycle frame, comprising
   a scale of failure points for a predetermined construction of the bicycle frame;
   a stand configured with an internal void and a mounting plate for securing a motor thereto,
   a mounting assembly operably coupled to said stand for securing the bicycle frame thereto, said mounting assembly being disposed above said mounting plate and motor;
   a transmission assembly operably coupled to said motor so as to gear-down revolutions of said motor in a ratio to simulate bicycle conditions;
   a crank assembly comprising pedal arms operably connected to said transmission assembly, each of said pedal arms being connected at one end to said transmission assembly in a fixed angular position and at the other end to a connector bar mounted by a pivot to a square mount attached to said stand below a bottom bracket of the bicycle frame mounted for testing; and
   one or more pistons operably connected to said pedal arms so as to provide macro and/or fine adjustments to connect said one or more pistons and said motor to the bicycle frame via each of said pedal arms,
   whereby when said motor is energized to provide a predetermined force input to each of said pedal arms so as to fatigue the bicycle frame such that the number of cycles to fatigue can be counted.

* * * * *